United States Patent
Weber et al.

(10) Patent No.: US 11,730,946 B2
(45) Date of Patent: Aug. 22, 2023

(54) FLOW ENHANCEMENT FOR CIRCULATORY SUPPORT DEVICE

(71) Applicant: Boston Scientific Scimed Inc., Maple Grove, MN (US)

(72) Inventors: Jan Weber, Maastricht (NL); Matthew Boyer, Columbia Heights, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 80 days.

(21) Appl. No.: 16/990,667

(22) Filed: Aug. 11, 2020

(65) Prior Publication Data

US 2021/0046231 A1 Feb. 18, 2021

Related U.S. Application Data

(60) Provisional application No. 62/885,499, filed on Aug. 12, 2019.

(51) Int. Cl.
| | |
|---|---|
| *A61M 60/221* | (2021.01) |
| *A61M 60/812* | (2021.01) |
| *A61M 60/122* | (2021.01) |
| *A61M 60/81* | (2021.01) |
| *A61M 60/857* | (2021.01) |
| *A61M 60/419* | (2021.01) |
| *A61M 60/274* | (2021.01) |

(52) U.S. Cl.
CPC .......... *A61M 60/81* (2021.01); *A61M 60/221* (2021.01); *A61M 60/812* (2021.01); *A61M 60/857* (2021.01); *A61M 60/274* (2021.01); *A61M 60/419* (2021.01); *A61M 2206/12* (2013.01)

(58) Field of Classification Search
CPC .. A61M 60/81; A61M 60/221; A61M 60/857; A61M 60/812; A61M 2206/12
See application file for complete search history.

(56) References Cited

U.S. PATENT DOCUMENTS

| 9,433,713 | B2 | 9/2016 | Corbett et al. | |
|---|---|---|---|---|
| 2003/0187322 | A1* | 10/2003 | Siess | A61M 60/419 600/16 |
| 2006/0161095 | A1* | 7/2006 | Aboul-Hosn | A61M 60/422 604/9 |
| 2008/0103591 | A1* | 5/2008 | Siess | A61M 60/205 623/3.13 |
| 2013/0303831 | A1* | 11/2013 | Evans | A61M 60/237 600/16 |

* cited by examiner

*Primary Examiner* — Pamela M. Bays
(74) *Attorney, Agent, or Firm* — Faegre Drinker Biddle & Reath LLP (57) ABSTRACT

An inlet tube of a circulatory support device includes a first end configured to receive incoming blood and a second end coupled to a first end of a blood pump. A lumen extends from the first end to the second end, and a spiral feature is disposed within the lumen and configured to support a spiral flow of the incoming blood.

8 Claims, 5 Drawing Sheets

FLOW ENHANCEMENT FOR CIRCULATORY SUPPORT DEVICE

CROSS REFERENCE TO RELATED APPLICATION

This application claims priority to Provisional Application No. 62/885,499, filed Aug. 12, 2019, which is herein incorporated by reference in its entirety.

TECHNICAL FIELD

The present disclosure relates to circulatory support devices. More specifically, the disclosure relates to flow enhancements in circulatory support devices.

BACKGROUND

Circulatory support devices such as blood pumps provide circulatory support. Typically, a circulatory support device includes a blood pump having an inlet coupled thereto. The inlet includes flexible tubing that receives blood into a first end and is coupled, at a second end, to a first end of a blood pump housing. An inlet guide having radially oriented blades is often disposed in the first end of the blood pump housing.

As blood flows into the device, the flow from the inlet tubing to the blood pump is moving in an axial direction, while the impeller of the blood pump introduces an almost circular flow (spiraling toward a second end of the blood pump). The inlet tubing is typically curved in the aorta toward the ventricle, which may result in turbulence. Additionally, the immediate transition from an axial flow to a circular flow directly after the inlet guide can create shear stress.

SUMMARY

In an Example 1, a circulatory support device comprises a blood pump; an inlet tube having a first end configured to receive incoming blood and a second end coupled to a first end of the blood pump, the inlet tube comprising a lumen extending from the first end to the second end; and a spiral feature disposed within the lumen and configured to support a spiral flow of the incoming blood.

In an Example 2, the circulatory support device of Example 1, wherein the spiral feature is disposed within the flow of incoming blood in the inlet tube.

In an Example 3, the circulatory support device of Example 2, wherein the spiral feature is at least approximately centrally located within the lumen of the inlet tube and comprises a first spiral wire, a second spiral wire, and an expandable membrane disposed between the first and second spiral wires.

In an Example 4, the circulatory support device of Example 1, wherein the spiral feature is disposed on the outside of the flow of incoming blood in the inlet tube.

In an Example 5, the circulatory support device of Example 4, the spiral feature comprising a spiral flange extending from an inner surface of the inlet tube.

In an Example 6, the circulatory support device of Example 5, wherein a pitch of the spiral flange decreases in the direction of the pump housing to support an increase of the fluid rotation.

In an Example 7, the circulatory support device of either of Examples 5 or 6, wherein the spiral flange comprises an insert configured to be removeably disposed within the lumen.

In an Example 8, the circulatory support device of either of Examples 5 or 6, wherein the spiral flange is integrated with the inner surface of the inlet tube.

In an Example 9, the circulatory support device of Example 4, the spiral feature comprising a spiral wire disposed adjacent an inner surface of the inlet tube.

In an Example 10, the circulatory support device of Example 9, further comprising an expandable membrane disposed between the spiral wire and the inner surface of the inlet tube.

In an Example 11, the circulatory support device of any of Examples 1-10, wherein the blood pump comprises: a pump housing comprising a first end and a second end, wherein the second end of the inlet tube is coupled to an outside of the first end of the pump housing; and an inlet guide disposed within the first end of the pump housing, the inlet guide comprising a plurality of stationary blades, wherein each of the plurality of stationary blades extends from a center support to an inner wall of the pump housing and is oriented at an angle with respect to the chamber so as to support a spiral flow of blood entering the blood pump.

In an Example 12, the circulatory support device of Example 11, wherein the pump housing further includes: a plurality of outflow ports; a plurality of housing outflow struts, wherein each of the plurality of housing outflow struts is disposed between the outflow ports of a pair of adjacent outflow ports, and wherein each of the plurality of housing outflow struts has an associated curved inner surface configured to support a spiral flow of blood out of the plurality of outflow ports.

In an Example 13, the circulatory support device of Example 12, further comprising a strut insert comprising a strut insert body configured to be disposed within the pump housing, and a plurality of insert struts, wherein each of the plurality of insert struts is configured to be disposed adjacent one of the housing outflow struts when the strut insert is disposed within the pump housing, wherein each of the plurality of insert struts includes the associated curved inner surface.

In an Example 14, a circulatory support device comprises an inlet tube having a first end configured to receive incoming blood, the inlet tube comprising a lumen extending through the inlet tube; and a blood pump, comprising: a pump housing comprising a first end and a second end, wherein a second end of the inlet tube is coupled to an outside of the first end of the pump housing; a plurality of outflow ports; and a plurality of housing outflow struts, wherein each of the plurality of housing outflow struts is disposed between the outflow ports of a pair of adjacent outflow ports, wherein each of the plurality of housing outflow struts has an associated curved inner surface configured to support a spiral flow of blood out of the plurality of outflow ports.

In an Example 15, the circulatory support device of Example 11, further comprising a strut insert comprising a strut insert body configured to be disposed within the pump housing, and a plurality of insert struts, wherein each of the plurality of insert struts is configured to be disposed adjacent one of the housing outflow struts when the strut insert is disposed within the pump housing, wherein each of the plurality of insert struts includes the associated curved inner surface.

In an Example 16, a circulatory support device comprises: a blood pump; an inlet tube having a first end configured to receive incoming blood and a second end coupled to a first end of the blood pump, the inlet tube comprising a lumen extending from the first end to the second end; and a spiral feature disposed within the lumen and configured to support a spiral flow of the incoming blood.

In an Example 17, the circulatory support device of Example 16, wherein the spiral feature is disposed within the flow of incoming blood in the inlet tube.

In an Example 18, the circulatory support device of Example 17, wherein the spiral feature is at least approximately centrally located within lumen of the inlet tube and comprises a first spiral wire, a second spiral wire, and an expandable membrane disposed between the first and second spiral wires.

In an Example 19, the circulatory support device of Example 16, wherein the spiral feature is disposed on the outside of the flow of incoming blood in the inlet tube.

In an Example 20, the circulatory support device of Example 19, the spiral feature comprising a spiral flange extending from an inner surface of the inlet tube.

In an Example 21, the circulatory support device of Example 20, wherein a pitch of the spiral flange decreases in the direction of the pump housing to support an increase of the fluid rotation.

In an Example 22, the circulatory support device of Example 20, wherein the spiral flange comprises an insert configured to be removeably disposed within the lumen.

In an Example 23, the circulatory support device of Example 20, wherein the spiral flange is integrated with the inner surface of the inlet tube.

In an Example 24, the circulatory support device of Example 19, the spiral feature comprising a spiral wire disposed adjacent an inner surface of the inlet tube.

In an Example 25, the circulatory support device of Example 24, further comprising an expandable membrane disposed between the spiral wire and the inner surface of the inlet tube.

In an Example 26, the circulatory support device of Example 16, wherein the blood pump comprises: a pump housing comprising a first end and a second end, wherein the second end of the inlet tube is coupled to an outside of the first end of the pump housing; and an inlet guide disposed within the first end of the pump housing, the inlet guide comprising a plurality of stationary blades, wherein each of the plurality of stationary blades extends from a center support to an inner wall of the pump housing and is oriented at an angle with respect to the chamber so as to support a spiral flow of blood entering the blood pump.

In an Example 27, the circulatory support device of Example 26, wherein the pump housing further includes: a plurality of outflow ports; a plurality of housing outflow struts, wherein each of the plurality of housing outflow struts is disposed between the outflow ports of a pair of adjacent outflow ports, and wherein each of the plurality of housing outflow struts has an associated curved inner surface configured to support a spiral flow of blood out of the plurality of outflow ports.

In an Example 28, the circulatory support device of Example 27, further comprising a strut insert comprising a strut insert body configured to be disposed within the pump housing, and a plurality of insert struts, wherein each of the plurality of insert struts is configured to be disposed adjacent one of the housing outflow struts when the strut insert is disposed within the pump housing, wherein each of the plurality of insert struts includes the associated curved inner surface.

In an Example 29, a circulatory support device, comprising: an inlet tube having a first end configured to receive incoming blood, the inlet tube comprising a lumen extending through the inlet tube; and a blood pump, comprising: a pump housing comprising a first end and a second end, wherein a second end of the inlet tube is coupled to an outside of the first end of the pump housing; a plurality of outflow ports; and a plurality of housing outflow struts, wherein each of the plurality of housing outflow struts is disposed between the outflow ports of a pair of adjacent outflow ports, wherein each of the plurality of housing outflow struts has an associated curved inner surface configured to support a spiral flow of blood out of the plurality of outflow ports.

In an Example 30, the circulatory support device of Example 29, further comprising a strut insert comprising a strut insert body configured to be disposed within the pump housing, and a plurality of insert struts, wherein each of the plurality of insert struts is configured to be disposed adjacent one of the housing outflow struts when the strut insert is disposed within the pump housing, wherein each of the plurality of insert struts includes the associated curved inner surface.

In an Example 31, the circulatory support device of Example 29, further comprising a spiral feature disposed within the lumen and configured to support a spiral flow of the incoming blood.

In an Example 32, the circulatory support device of Example 31, wherein the spiral feature is disposed within the flow of incoming blood in the inlet tube.

In an Example 33, the circulatory support device of Example 31, wherein the spiral feature is disposed on the outside of the flow of incoming blood in the inlet tube.

In an Example 34, an inlet tube of a circulatory support device comprises a first end configured to receive incoming blood and a second end coupled to a first end of the blood pump; a lumen extending from the first end to the second end; and a spiral feature disposed within the lumen and configured to support a spiral flow of the incoming blood.

In an Example 35, the inlet tube of Example 34, wherein the spiral feature is disposed within the flow of incoming blood in the inlet tube.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

DETAILED DESCRIPTION

Figure 1A:
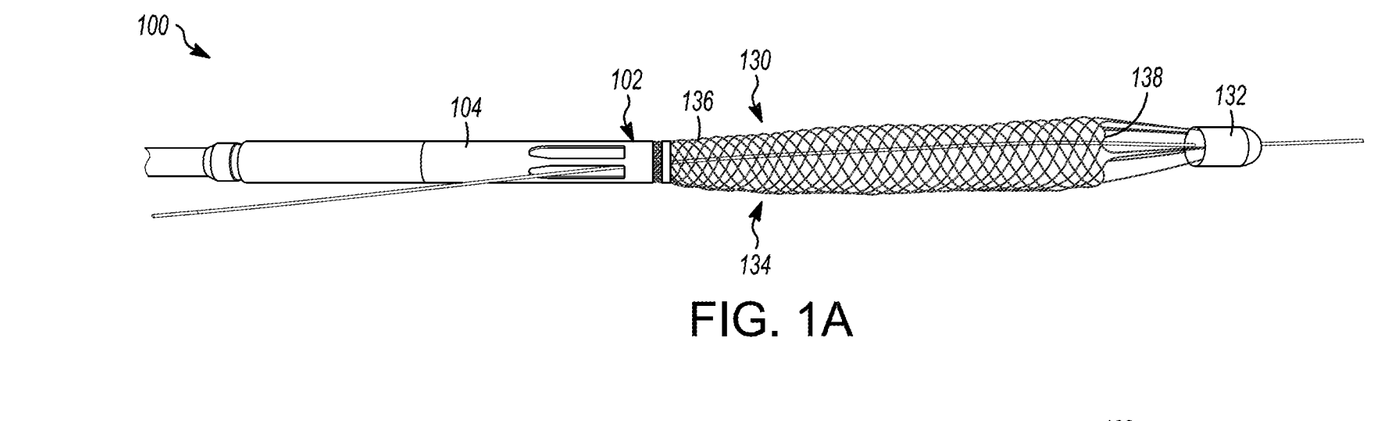
FIG. 1A depicts a perspective side view of an illustrative mechanical circulatory support device, in accordance with embodiments of the subject matter disclosed herein.
Figure 1B:
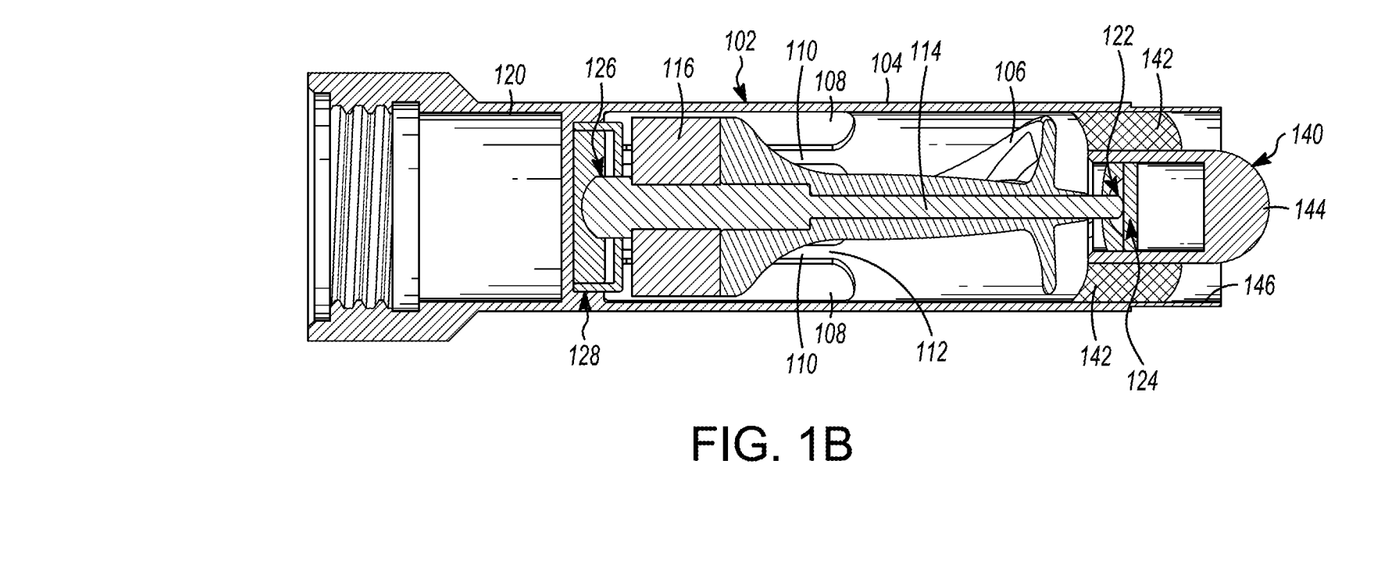
FIG. 1B is a cross-sectional side view of a portion of the illustrative mechanical circulatory support device depicted in FIG. 1A, in accordance with embodiments of the subject matter disclosed herein.

FIG. 1A depicts a perspective side view of an illustrative mechanical circulatory support device 100, and FIG. 1B is a cross-sectional side view of a portion of the illustrative mechanical circulatory support device depicted in FIG. 1A, in accordance with embodiments of the subject matter disclosed herein. As shown in FIGS. 1A and 1B, the circulatory support device 100 includes a blood pump 102 disposed within a pump housing 104. The pump 102 includes an impeller 106 to provide a flow of blood through the device 100.

The pump housing 104 includes a number of outflow ports 108 defined therein. As shown in FIG. 1B, the pump housing 104 includes a number of housing outflow struts 110, where each housing outflow strut 110 is disposed between the outflow ports 108 of a pair of adjacent outflow ports 108, and wherein each of the plurality of housing outflow struts 110 has an associated curved inner surface 112 configured to support a spiral flow of blood out of the plurality of outflow ports 108.

As shown in FIG. 1B, the blood pump 102 includes a drive shaft 114 coupled to the impeller 106 and configured to rotate with the impeller 106. As shown, the drive shaft 114 is at least partially disposed within the impeller 106. In embodiments, the drive shaft 114 may be made of any number of different rigid materials such as, for example, steel, titanium alloys, cobalt chromium alloys, nitinol, high-strength ceramics, and/or the like. An impeller rotor 116 is coupled to, and at least partially surrounds, the drive shaft 114. The impeller rotor 116 may be any type of magnetic rotor capable of being driven by a stator (not shown) that is part of a motor 120. In this manner, as a magnetic field is applied to the impeller rotor 116 by the stator in the motor 120, the rotor 116 rotates, causing the drive shaft 114 and impeller 106 to rotate.

As shown, the impeller is maintained in its orientation by the drive shaft 114, which is retained, at a first end 122, by a first bearing assembly 124 and, at a second end 126, by a second bearing assembly 128. According to embodiments, the first bearing assembly 124 and the second bearing assembly 128 may include different types of bearings. According to embodiments, the first bearing assembly 124 and/or the second bearing assembly 128 may include lubrication, while, in other embodiments, one and/or the other may not include lubrication. Various embodiments of bearing technology are described herein with respect to the first and second bearing assemblies 124 and 128.

As shown in FIG. 1A, the device includes an expandable inlet tube 130 having a first end 132 configured to receive incoming blood and a second end 134 coupled to a first end 136 of the blood pump 102. A lumen 138 is disposed through the inlet tube 130, extending from the first end 132 to the second end 134. As discussed in further detail below, a spiral feature may be disposed within the lumen 138 and configured to support a spiral flow of the incoming blood. In embodiments, the spiral feature may extend from the first end 132 to the second end 134.

In embodiments, the first bearing assembly 124 may include, be included in, be coupled to, or be otherwise associated with an inlet guide 140. For example, the first end 136 of the pump housing 104. In embodiments, the inlet guide 140 may include a number of stationary blades 142, each extending from a center support 144 to an inner wall 146 of the pump housing 104. According to embodiments, each blade 142 is curved and oriented at an angle with respect to the axis of the lumen 138 so as to support a spiral flow of blood entering the blood pump.

The illustrative circulatory support device 100 shown in FIGS. 1A and 1B is not intended to suggest any limitation as to the scope of use or functionality of embodiments of the present disclosure. The illustrative circulatory support device 100 also should not be interpreted as having any dependency or requirement related to any single component or combination of components illustrated therein. Additionally, various components depicted in FIGS. 1A and 1B may be, in embodiments, integrated with various ones of the other components depicted therein (and/or components not illustrated), all of which are considered to be within the ambit of the present disclosure.

Figure 2:
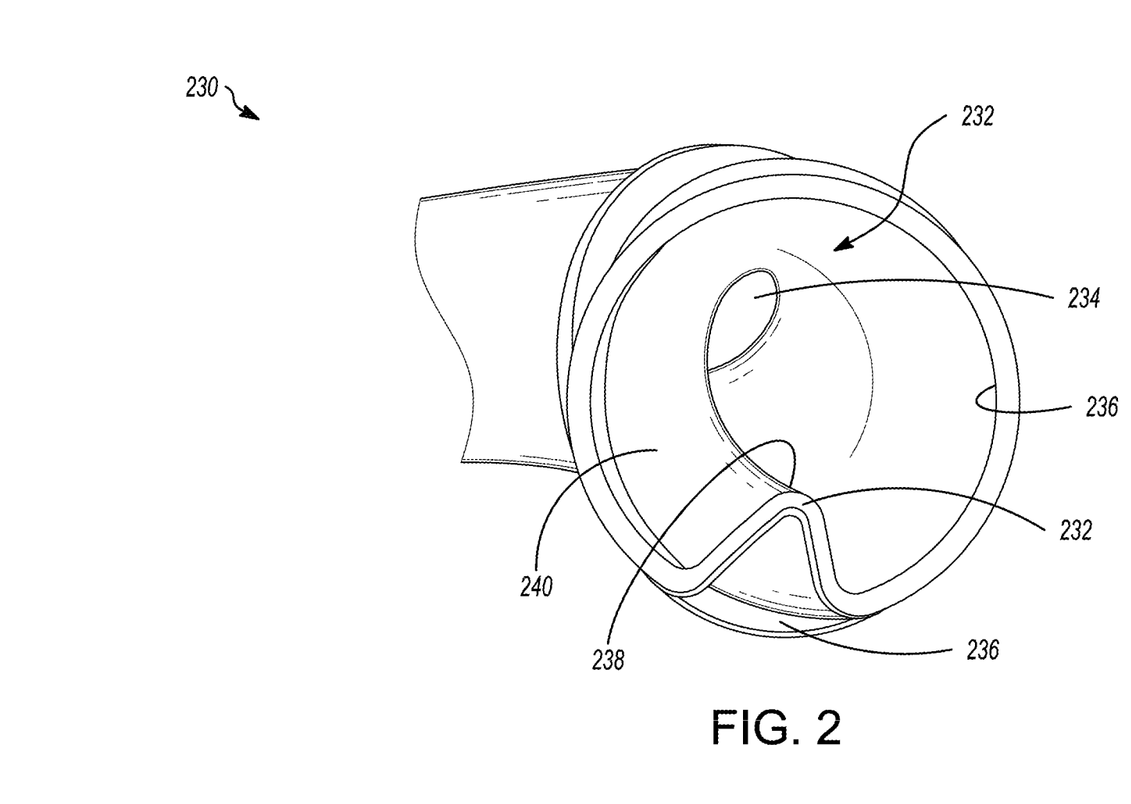
FIG. 2 depicts a perspective view of a portion of an inlet tube of an illustrative mechanical circulatory support device, in accordance with embodiments of the subject matter disclosed herein.

FIG. 2 depicts a perspective view of a portion of an inlet tube 230 of an illustrative mechanical circulatory support device, in accordance with embodiments of the subject matter disclosed herein. According to embodiments, the circulatory support device may be, include, be similar to, or be included in the circulatory support device 100 depicted in FIGS. 1A and 1B, and the inlet tube 230 may be, or be similar to, the inlet tube 130 depicted in FIG. 1A. According to embodiments, a spiral feature 232 may be disposed within the lumen 234 defined in the inlet tube 230. In the embodiments depicted in FIG. 2, the spiral feature 232 is disposed on the outside of the fluid column within the tube 230.

According to embodiments, the spiral feature 232 may be configured to support a spiral flow of the incoming blood and may extend from a first end of the lumen 234 to a second end. As shown in FIG. 2, the spiral feature 232 may include a spiral flange extending from an inner surface 236 of the inlet tube 230. The spiral flange 232 includes an innermost edge 238 having a spiral configuration and disposed within the lumen, and a flange surface 240 extending between the innermost edge 238 and the inner surface 236 of the inlet tube 230. In embodiments, the spiral flange 232 may be integrated with the inner surface 236. In other embodiments, the spiral flange 232 may be affixed to the inner surface 236, removeably coupled thereto, and/or the like. According to embodiments, the spiral flange 232 includes an insert configured to be removeably disposed within the lumen. In embodiments, the flange may include a spiral wire that forms the innermost edge 238 and a flexible membrane that forms the flange surface 240.

In embodiments, a pitch of the spiral flange 232 decreases in the direction of the pump housing to support an increase of the fluid rotation. The height of the spiral flange (e.g., the distance from the inner surface 236 to the outermost edge of the spiral flange, where the outermost edge is the edge of the flange that is farthest from the inner surface 236) may change from the first end of the inlet tube 230 to the second end of the inlet tube 230 (e.g., from the first end 132 of the inlet tube 130 to the second end 134 of the inlet tube 130, depicted in FIG. 1A). In the case of the flange 232 including a spiral wire with a flexible membrane extending between the wire and the inner surface 236 of the inlet tube 230, the height of the spiral flange may be adjustable such as, for example, in response to blood flow, to support insertion of the flange within the tube 230, and/or the like. In embodiments, opposing flanges may contact each other at the center line to provide multiple (e.g., two or three or more) completely separate channels within the tube 230.

The illustrative inlet tube 230 shown in FIG. 2 is not intended to suggest any limitation as to the scope of use or functionality of embodiments of the present disclosure. The illustrative inlet tube 230 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3A:
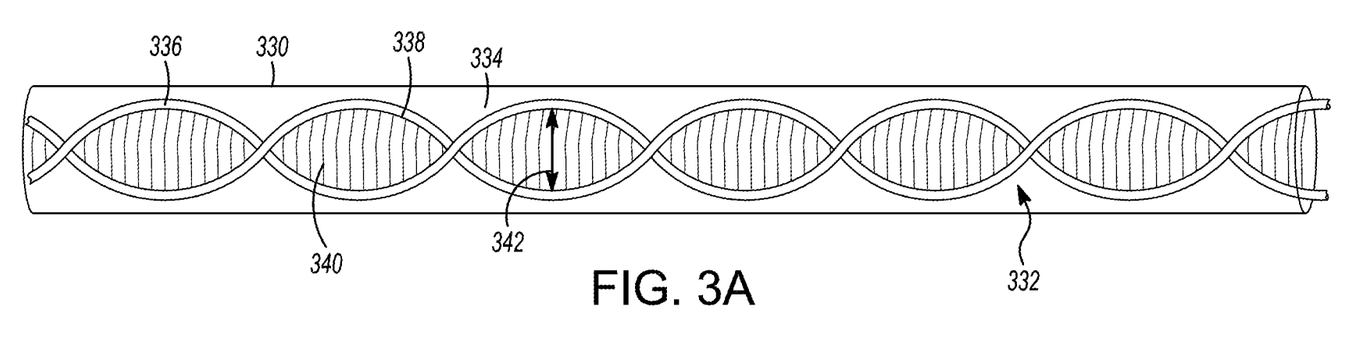
FIG. 3A depicts a partially cut-away schematic side view of a portion of another inlet tube of another illustrative mechanical circulatory support device, in accordance with embodiments of the subject matter disclosed herein.
Figure 3B:
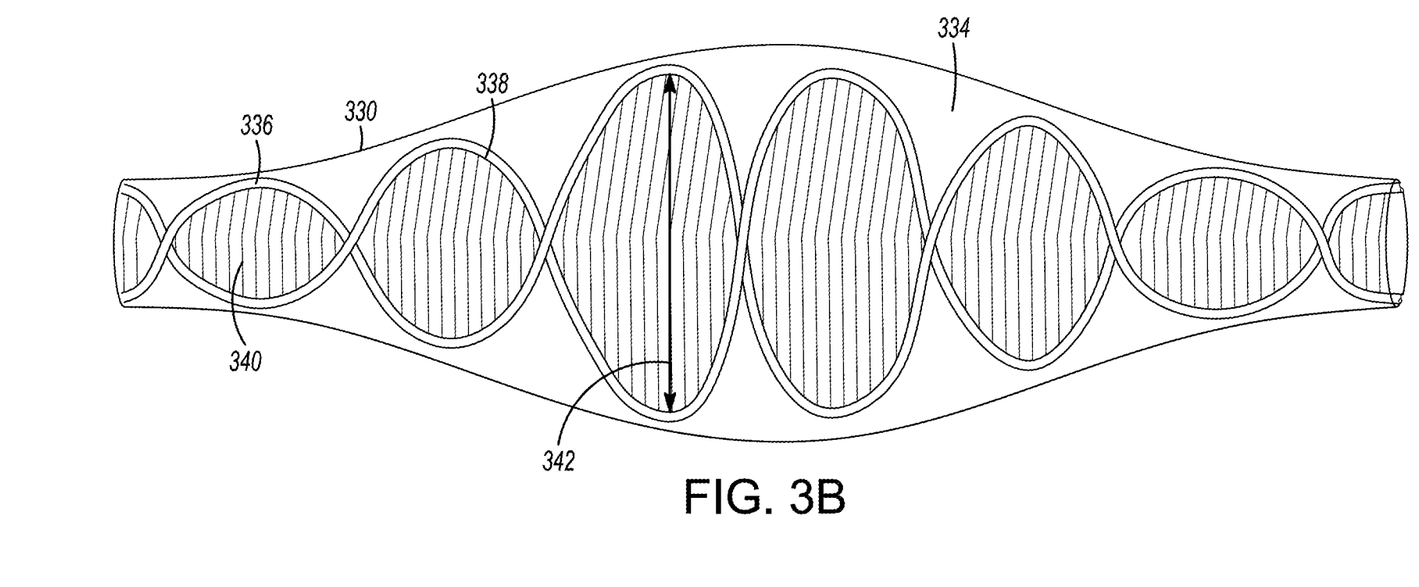
FIG. 3B depicts a partially cut-away schematic side view of the portion of the inlet tube depicted in FIG. 3A, in an expanded state, in accordance with embodiments of the subject matter disclosed herein.

FIGS. 3A and 3B depict partially cut-away schematic side views of a portion of another inlet tube 330 of another illustrative mechanical circulatory support device, in accordance with embodiments of the subject matter disclosed herein. According to embodiments, the circulatory support device may be, include, be similar to, or be included in the circulatory support device 100 depicted in FIGS. 1A and 1B, and the inlet tube 330 may be, or be similar to, the inlet tube 130 depicted in FIG. 1A. In the embodiments depicted in FIGS. 3A and 3B, spiral feature 332 is disposed within the flow of blood in the tube 330, and may be, for example, at least approximately centrally located in the lumen 334. According to embodiments, the tube 330 may include a spiral feature on the outside of the fluid column, as well (e.g., the spiral feature 232 depicted in FIG. 2). As shown, the spiral feature 332 may include a first spiral wire 336 and a second spiral wire 338 with a membrane 340 disposed between them. The spiral wires 336 and 338 may be made from metal and may be flexible or semi-rigid so that they can facilitate expansion of the spiral feature 332, and the membrane 340 may be made from an expandable elastic material. In this manner, as shown in FIGS. 3A and 3B, the diameter 342 of the spiral feature 332 may expand along at least a portion of the length of the spiral feature 332 during operation, and may be configured to be contracted during insertion.

The illustrative inlet tube 330 shown in FIGS. 3A and 3B is not intended to suggest any limitation as to the scope of use or functionality of embodiments of the present disclosure. The illustrative inlet tube 330 also should not be interpreted as having any dependency or requirement related to any single component or combination of components illustrated therein. Additionally, various components depicted in FIGS. 3A and 3B may be, in embodiments, integrated with various ones of the other components depicted therein (and/or components not illustrated), all of which are considered to be within the ambit of the present disclosure.

Figure 4A:
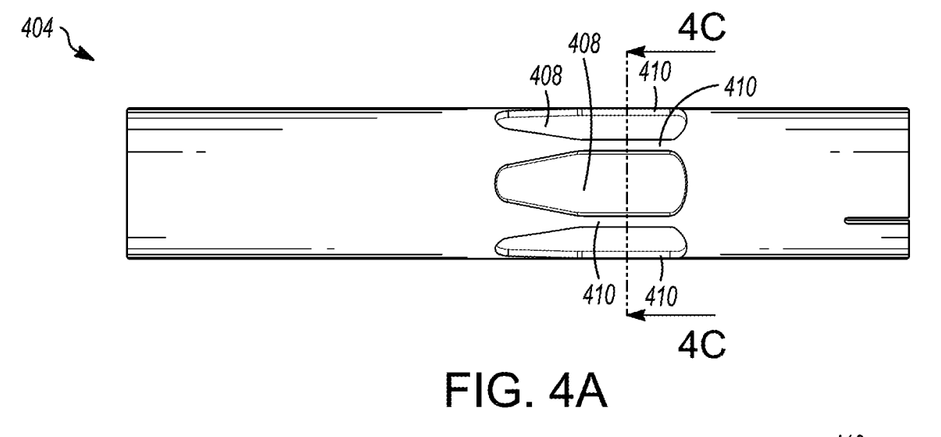
FIG. 4A depicts a side view of a portion of a blood pump housing of an illustrative mechanical circulatory support device, in accordance with embodiments of the subject matter disclosed herein.
Figure 4B:
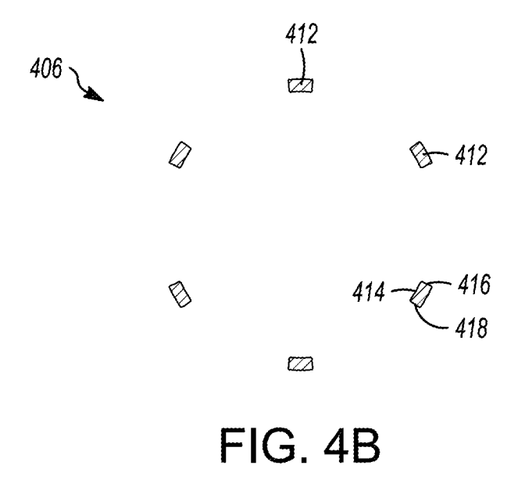
FIG. 4B is a cross-sectional view of an illustrative prior art blood pump housing.
Figure 4C:
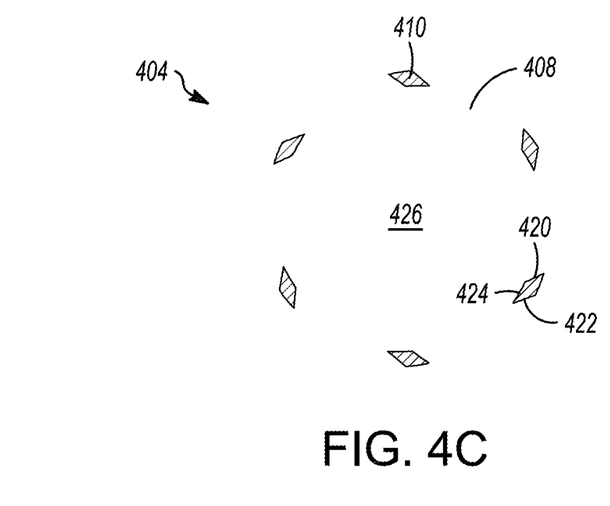
FIG. 4C is a cross-sectional view taken along the line 4C-4C of the illustrative blood pump housing 400 depicted in FIG. 4A, in accordance with embodiments of the subject matter disclosed herein.

FIG. 4A depicts a side view of a portion of a blood pump housing 404 of an illustrative mechanical circulatory support device, in accordance with embodiments of the subject matter disclosed herein. FIG. 4B is a cross-sectional view of an illustrative prior art blood pump housing 406; and FIG. 4C is a cross-sectional view taken along the line 4C-4C of the illustrative blood pump housing 404 depicted in FIG. 4A, in accordance with embodiments of the subject matter disclosed herein. According to embodiments, the circulatory support device may be, include, be similar to, or be included in the circulatory support device 100 depicted in FIGS. 1A and 1B; and, similarly, the blood pump housings 404 and 406 may be, or be similar to, the blood pump housing 104 depicted in FIGS. 1A and 1B.

According to embodiments, as shown, the pump housing 404 includes a number of outflow ports 408 and a number of housing outflow struts 410, where each of the housing outflow struts 410 is disposed between the outflow ports 408 of a pair of adjacent outflow ports 408. As shown in FIG. 4B, prior pump housings 406 include struts 412 having rectangular cross-sectional profiles. While the edges may be slightly rounded via electropolishing, they are not shaped to support the spiral outflow of fluid. Additionally, the inner surface 414 of each strut meets a first adjacent side surface 416 at an angle at least approximately equal to an angle at which the inner surface meets a second, opposite, side surface 418. These angles are approximately perpendicular. The shape of the prior art struts 410 causes turbulence and reduces flow efficiency.

According to embodiments, the outflow struts of the presently disclosed subject matter may be tapered and/or otherwise curved to reduce drag. In embodiments, this may be achieved by thickening and re-cutting the outflow ports 408. In embodiments, for example, as shown in FIG. 4C, the outflow ports 408 may be cut such that the struts 410 have angled side surfaces 420 and 422. According to embodiments, the angled side surfaces 420 and 422 may be configured to facilitate a spiral outflow of fluid from the blood pump housing. That is, for example, the inner surface 424 of each strut may be configured to meet a first adjacent side surface 420 at an angle that is different than an angle at which the inner surface 424 meets a second, opposite, side surface 422. According to embodiments, each of the plurality of housing outflow struts 410 may include an associated curved inner surface configured to support a spiral flow of blood out of the plurality of outflow ports 408. That is, for example, the associated inner surface may be curved convexly into the lumen 426. The curved inner surface may be integrated into the strut and/or provided by an insert, as shown in FIGS. 5A-5C.

The illustrative blood pump housing 404 shown in FIGS. 4A-4C is not intended to suggest any limitation as to the scope of use or functionality of embodiments of the present disclosure. The illustrative blood pump housing 404 also should not be interpreted as having any dependency or requirement related to any single component or combination of components illustrated therein. Additionally, various components depicted in FIGS. 4A-4C may be, in embodiments, integrated with various ones of the other components depicted therein (and/or components not illustrated), all of which are considered to be within the ambit of the present disclosure.

Figures 5A, 5B, 5C:
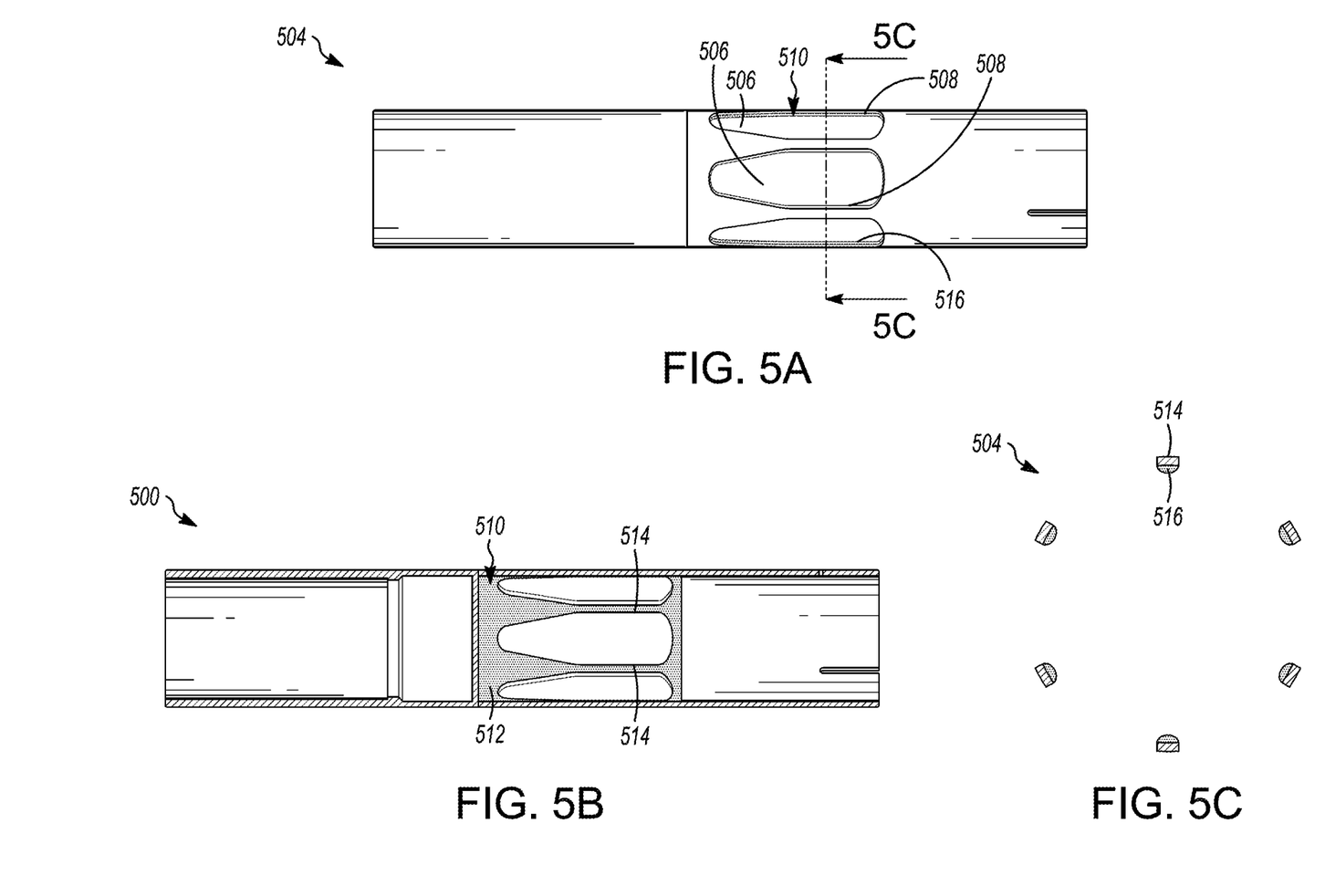
FIG. 5A depicts a side view of a portion of a blood pump housing of an illustrative mechanical circulatory support device, in accordance with embodiments of the subject matter disclosed herein.
FIG. 5B is a cross-sectional side view of the illustrative blood pump housing depicted in FIG. 5A, in accordance with embodiments of the subject matter disclosed herein.
FIG. 5C is a cross-sectional view taken along the line 5C-5C of the illustrative blood pump housing depicted in FIGS. 5A and 5B, in accordance with embodiments of the subject matter disclosed herein.

FIG. 5A depicts a side view of a portion of a blood pump housing 504 of an illustrative mechanical circulatory support device; FIG. 5B is a cross-sectional side view of the illustrative blood pump housing 504 depicted in FIG. 5A; and FIG. 5C is a cross-sectional view taken along the line 5C-5C of the illustrative blood pump housing 504 depicted in FIGS. 5A and 5B, in accordance with embodiments of the subject matter disclosed herein. According to embodiments, the circulatory support device may be, include, be similar to, or be included in the circulatory support device 100 depicted in FIGS. 1A and 1B; and the blood pump housing 504 may be, or be similar to, the pump housing 104 depicted in FIGS. 1A and 1B.

As is shown, primarily in FIGS. 5A-5C, the blood pump housing 504 includes a number of outflow ports 506 and a number of housing outflow struts 508, where each of the housing outflow struts 508 is disposed between the outflow ports 506 of a pair of adjacent outflow ports 506. As shown, a strut insert 510 may be disposed within the pump housing 504. The strut insert 510 includes a strut insert body 512 configured to be disposed within the pump housing 504, and a number of insert struts 514. According to embodiments, each of the insert struts 514 is configured to be disposed adjacent one of the housing outflow struts 510 when the strut insert 508 is disposed within the pump housing 504. Each of the insert struts 514 includes the associated curved inner surface 516 and, accordingly, is configured to facilitate supporting a spiral outflow of fluid through the outflow ports 506.

The illustrative blood pump housing 504 shown in FIGS. 5A-5C is not intended to suggest any limitation as to the scope of use or functionality of embodiments of the present disclosure. The illustrative blood pump housing 504 also should not be interpreted as having any dependency or requirement related to any single component or combination of components illustrated therein. Additionally, various components depicted in FIGS. 5A-5C may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A circulatory support device, comprising:
   an inlet tube having a first end configured to receive incoming blood, the inlet tube comprising a lumen extending through the inlet tube; and
   a blood pump, comprising:
      a pump housing comprising a first end and a second end, wherein a second end of the inlet tube is coupled to an outside of the first end of the pump housing;
      a plurality of outflow ports;
      a plurality of housing outflow struts, wherein each of the plurality of housing outflow struts is disposed between the outflow ports of a pair of adjacent outflow ports, wherein at least some of the plurality of housing outflow struts extend longitudinally relative to the pump housing;
      an impeller disposed in the pump housing and being rotatable to cause blood to flow through the circulatory support device; and
      a strut insert configured to permit blood to flow therethrough, the strut insert comprising a strut insert body, the strut insert body comprising a proximal portion disposed within the pump housing and a distal portion disposed within the pump housing, and the strut insert further comprising a plurality of insert struts disposed within the pump housing, wherein each of the plurality of insert struts is disposed adjacent one of the housing outflow struts, wherein at least some of the plurality of insert struts each extends longitudinally relative to the pump housing and from the proximal portion of the strut insert body to the distal portion of the strut insert body, and wherein the at least some of the plurality of insert struts includes a curved inner surface configured to support a spiral flow of blood out of the plurality of outflow ports.

2. The circulatory support device of claim 1, further comprising a spiral feature disposed within the lumen of the inlet tube and configured to support a spiral flow of the incoming blood.

3. The circulatory support device of claim 2, wherein the spiral feature is disposed within the flow of incoming blood in the inlet tube.

4. The circulatory support device of claim 2, wherein the spiral feature is disposed on the outside of the flow of incoming blood in the inlet tube.

5. A circulatory support device, comprising:
   an inlet tube having a first end configured to receive incoming blood, the inlet tube comprising a lumen extending through the inlet tube; and
   a blood pump, comprising:

a pump housing comprising a first end and a second end, wherein a second end of the inlet tube is coupled to an outside of the first end of the pump housing;

a plurality of outflow ports;

a plurality of housing outflow struts, wherein each of the plurality of housing outflow struts is disposed between the outflow ports of a pair of adjacent outflow ports, wherein at least some of the plurality of housing outflow struts extend longitudinally relative to the pump housing; and a strut insert configured to permit blood to flow therethrough, the strut insert comprising a strut insert body, the strut insert body comprising a proximal portion disposed within the pump housing and a distal portion disposed within the pump housing, and the strut insert further comprising a plurality of insert struts disposed within the pump housing, wherein each of the plurality of insert struts is aligned and in contact with one of the housing outflow struts, wherein at least some of the plurality of insert struts each extends longitudinally relative to the pump housing and from the proximal portion of the strut insert body to the distal portion of the strut insert body, and wherein the at least some of the plurality of insert struts includes a curved inner surface configured to support a spiral flow of blood out of the plurality of outflow ports.

6. The circulatory support device of claim 5, further comprising a spiral feature disposed within the lumen of the inlet tube and configured to support a spiral flow of the incoming blood.

7. The circulatory support device of claim 6, wherein the spiral feature is disposed within the flow of incoming blood in the inlet tube.

8. The circulatory support device of claim 6, wherein the spiral feature is disposed on the outside of the flow of incoming blood in the inlet tube.

* * * * *